United States Patent [19]

Gironda et al.

[11] Patent Number: 5,384,326
[45] Date of Patent: Jan. 24, 1995

[54] GIRONDALONES

[75] Inventors: Kevin F. Gironda, Alpha, N.J.; Peter Osei-Gyimah, Horsham; Barry C. Lange, Lansdale, both of Pa.

[73] Assignee: Rohm and Haas Company, Philadelphia, Pa.

[21] Appl. No.: 794,753

[22] Filed: Nov. 12, 1991

[51] Int. Cl.$^6$ ............... C07D 275/03; C07D 275/04; A01N 43/80
[52] U.S. Cl. .................... 514/372; 514/373; 548/119; 548/209; 548/213
[58] Field of Search .............. 548/209, 213, 119; 514/372, 373

[56] References Cited

U.S. PATENT DOCUMENTS

| | | | |
|---|---|---|---|
| 3,544,580 | 12/1970 | Lewis et al. | 548/213 |
| 3,706,757 | 12/1972 | Lewis et al. | 548/213 |
| 3,761,488 | 9/1973 | Lewis et al. | 548/213 |
| 3,835,150 | 9/1974 | Lewis et al. | 548/213 |
| 4,105,431 | 8/1978 | Lewis et al. | 548/213 |
| 4,165,318 | 8/1979 | Greenfield et al. | 548/213 |
| 4,165,318 | 8/1979 | Greenfield et al. | 548/213 |
| 4,167,575 | 9/1979 | Miller et al. | 548/213 |

FOREIGN PATENT DOCUMENTS

| | | |
|---|---|---|
| 393948 | 10/1990 | European Pat. Off. . |
| 435439 | 7/1991 | European Pat. Off. . |

OTHER PUBLICATIONS

March, Advanced Organic Chemistry, Wiley & Sons 1985, pp. 345–346.

*Primary Examiner*—Mary C. Lee
*Attorney, Agent, or Firm*—Michael B. Fein

[57] ABSTRACT

Girondalones of the formula I useful as microbicides

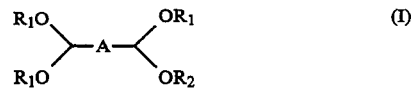

wherein
  A is a residue of a dialdehyde;
  $R_1$ is independently selected from the group consisting of $R_2$ and $(C_1-C_{18})$alkyl and;
  $R_2$ is

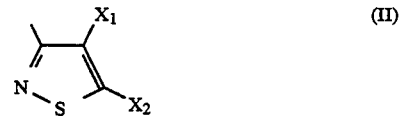

wherein
  (i) $X_1$ and $X_2$ can be joined to form a 5 or 6 membered fused carbocyclic ring, said ring being saturated, unsaturated, or aromatic; or
  (ii) $X_1$=Cl, H, methyl, or Br; and
  $X_2$=H, Cl, or Br.

4 Claims, No Drawings

GIRONDALONES

BACKGROUND OF THE INVENTION

1. Field of the Invention

This invention relates to the field of antimicrobial compounds and compositions. In particular, it relates to new isothiazolyl compounds which are usefull as microbicides and are referred to as girondalones.

2. Description of the Prior Art

Lewis et al., U.S. Pat. Nos. 3,761,488; 3,544,580; 3,835,150; 3,706,757; and 4,105,431, all assigned to Rohm and Haas Co., the same assignee as the present invention, disclose 3-isothiazolone compounds. Willingham et al. in U.S. Ser. Nos. 438,816, filed Nov. 17, 1989 and 601,964, filed Oct. 22, 1990, both assigned to Rohm and Haas Company, disclose stabilizing said isothiazolone compounds with carbonyl compounds. Other stabilization methods for isothiazolones are disclosed in a series of patents assigned to the same assignee.

It has been a problem in the art to find an ideal stabilization method for the 3-isothiazolone compounds which are outstanding anti-microbial compounds but are chemically and thermally unstable unless one of the aforementioned stabilization systems is used. Another problem with the 3-isothiazolones is that they can be skin sensitizers under certain conditions.

SUMMARY OF THE INVENTION

It was an object of the present invention to provide a new stabilization method for 3-isothiazolone compounds which improved upon prior methods. It was another object to provide a way to decrease the skin sensitization potential of the 3-isothiazolones. In seeking to achieve these objectives, a new class of compounds was unexpectedly discovered which not only achieves these objectives, but have additional advantages in their own right.

These objects and others which will become apparent from the following disclosure are achieved by the present invention which in one aspect comprises girondalone compounds of the formula

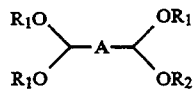
(I)

wherein
A is a residue of a dialdehyde; of the formula OH-C—A—CHO
$R_1$ is independently selected from the group consisting of $R_2$ and $(C_1-C_{18})$alkyl and;
$R_2$ is

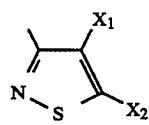
(II)

wherein
(i) $X_1$ and $X_2$ can be joined to form a 5 or 6 membered fused carbocyclic ring, said ring being saturated, unsaturated, or aromatic; or
(ii) $X_1$=Cl, H, methyl, or Br; and
$X_2$=H, Cl, or Br.

In another aspect the invention comprises preparing a girondalone compound of formula I by a method comprising reacting a compound of the formula

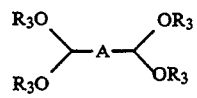
(III)

wherein $R_3$ is $(C_1-C_{18})$alkyl, with 3-hydroxyisothiazole or a substituted derivative thereof of the formula

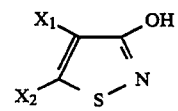
(IV)

DETAILED DESCRIPTION OF THE INVENTION AND THE PREFERRED EMBODIMENTS

The preferred method of preparing the girondalone compounds of the invention is as set forth in the Summary. It is preferred to conduct the reaction by using heat and in the presence of a weak acid such as propionic acid. The product is preferably a mixture of compounds of formula I with some compounds having no $R_1=R_2$, some having one $R_1=R_2$, and some having two or three $R_1=R_2$.

Examples of suitable dialdehydes represented by A are glutaraldehyde; malonaldehyde; succinaldehyde; octanedial; 2,2-sulfonyl-bis-acetaldehyde; 2,2-oxy-bis-acetaldehyde; 2,2-alkylphosphine oxide-bis-acetaldehyde; succinic acid-2,3-bis-acetaldehyde; phthaldehyde; homophthalaldehyde; 4-octenedial; 2-cylopentene-1;4-dial, and glyoxal. A special case is when A represents the residue of glyoxal in which case the girondalone compounds of formula (I) can be represented by formula (V) as follows:

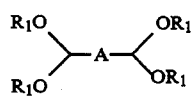
(V)

The girondalone compounds of the invention are especially active and efficient antimicrobial compounds. Among the preferred compounds of formula are the following:

1.) 1,3,3-Trimethoxy-1-(5-chloro-isothiazoloxy-3yl) propane;
2.) 1,3-Dimethoxy-1,3-bis-(5-chloro-isothiazoloxy-3-yl) propane;
3.) 1,3,3-Trimethoxy-1-(isothiazoloxy-3-yl) propane; and
4.) 1,3-Dimethoxy-1,3-bis-(isothiazoloxy-3-yl) propane The melting point of compound 2 was 57° C. Compounds 1, 3 and 4 were oils.

The following lists specific industries and applications of the girondalone compounds and compositions.

| Industry | Application |
| --- | --- |
| Adhesives, sealants | adhesives |
| | caulks |
| | sealants |
| Agriculture/food chain | adjuvant preservation |
| | agricultural active ingredient |

| Industry | Application |
|---|---|
| | agricultural chemical preservative |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt / concrete |
| | cement modifiers |
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| Formulated consumer & industrial products | air fresheners |
| | fabric softeners |
| | hand cleaners |
| | polishes, floor, furniture, shoe |
| | sponges & towelettes |
| | spray strach |
| | waxes |
| Industrial processing, misc | dry cleaning fluids preservation |
| | electrodeposition paint, baths, rinses |
| | electrodeposition pretreatment, post rinses |
| | industrial fluids preservation |
| | pasteurization baths |
| | process aid preservation |
| Industrial water treatment | air washers |
| | cooling towers |
| | cooling water |
| | water cooling |
| Laundry | household laundry products |
| | laundered goods |
| | laundry rinse water |
| | pre-washers |
| | sanitizers-laundry |
| | removers, spot & stain |
| Leather, leather products | leather and hide |
| | leather and hide products |
| Lubricants, hydraulic aids | automotive lubricants and fluids |
| | conveyor lubricants |
| | greases |
| | hydraulic fluids |
| | hydraulic oils |
| | lubricants |
| Medical devices | diagnostic enzymes |
| | diagnostic kits |
| | medical devices |
| Metalworking & related app's | cutting fluids |
| | metal cleaning |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |

| Industry | Application |
|---|---|
| Paints and coatings | coating emulsions |
| | paints |
| Paper and wood pulp, their products | absorbant materials of paper and wood pulp |
| | packaging materials of paper and wood pulp |
| | paper |
| | paper products |
| | paper treatment |
| | soap wrap |
| | wood pulp |
| | wood pulp products |
| Paper mill | paper mill slimicides |
| | pulp and paper slurries |
| Petroleum refining, fuels aviation | aviation fuels (jet fuel, gas) |
| | burner, diesel and turbine fuel oils |
| | coal slurries |
| | diesel fuel additives |
| | diesel fuels |
| | fuels |
| | gasoline |
| | heating oils |
| | hydrocarbons |
| | kerosene |
| | liquefied petroleum gas |
| | petrochemical feedstocks |
| | petroleum products, storage, transportation and production |
| | recycled petroleum products |
| | residual fuel oils |
| | turbine oils |
| Photographic chemicals and process | photographic processing - wash water, rinses |
| | photoplate processing chemicals (developers, stabilizers etc) |
| Printing | fountain solutions (printing) |
| | ink components (pigments, resins, solvents, etc) |
| | inks |
| Sanitizers (active) | sanitizers |
| | sanitizers-dairy |
| | sanitizers-dental |
| | sanitizers-fermentation |
| | sanitizers-food preparation |
| | sanitizers-food processing |
| | sanitizers-medical |
| | sanitizers-rendering |
| | sanitizers-veterinary |
| Soaps, detergents, cleaners | cleaners |
| | detergents, hand automatic laundry, other |
| | household cleaners |
| | industrial cleaners |
| | liquid soaps, hand, dish, laundry |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |
| | fibers |
| | geotextiles |
| | goods made of textiles |
| | knitted fabrics |
| | nets |
| | nonwoven fabrics |
| | rope |

| Industry | Application |
|---|---|
| | rugs |
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | textile processing fluids |
| Therapeutic (active or preservative) | animal health/veterinary |
| | aquaculture |
| | dental |
| | human health |
| | pharmaceutical /therapeutic |
| Water purification | charcoal beds |
| | deionization resins |
| | filters |
| | membranes |
| | reverse osmosis membranes |
| | ultrafilters |
| | water purification |
| | water purification pipes, tubing |
| Wood applications | lazures (wood stains) |
| | wood |
| | wood products |
| Miscellaneous | alcohols |
| | bedding incorporating water or gels |
| | ceramic |
| | contact lens cases-leaching |
| | electronic circuitry |
| | electronics chemicals |
| | enzymes-food production |
| | enzymes-industrial |
| | gel cushions |
| | laboratory reagents |
| | marine antifoulants |
| | mildewcides |
| | mining applications |
| | natural rubber latex |
| | oil field applications |
| | pipes |
| | plastics |
| | polymer systems |
| | polymers and resins (synthetic and natural) |
| | reagent preservation |
| | rubber |
| | rubber products |
| | skin remover |
| | solid protective/decorative films |
| | swimming pools |
| | waste treatment |
| | water beds |

The amounts of the girondalone compound to be used depend on the application. The useful amounts for a particular application are similar to amounts used for other microbicidal compounds.

The girondalone compound can be used in combination with other microbicides. The term "microbicide" is considered equivalent to "antimicrobial" as used herein.

Suitable methods of application of girondalone compounds of formula I to control fungi, bacteria, algae, viruses, yeasts, and the like are in amounts and with carriers, etc., as are well known in the art.

The following examples are presented to illustrate a few embodiments of the invention, but are not to be considered as limiting.

EXAMPLE 1

1,3,3-Trimethoxy-1-(isothiazoloxy-3-yl) Propane and 1,3-Dimethoxy-1,3bis-(isothiazoloxy,3-yl) Propane To a stirred mixture of 3-hydroxy-isothiazole (6 g, 0.0594 m) and malonaldehyde bis(dimethyl acetal)(8.24g., 0.0502m), propionic acid (0.2 g., 0.0027 m) was added.

The mixture was heated at 100 ° C. with stirring for 14 hours, cooled, and poured into saturated sodium bicarbonate solution. The mixture was extracted with ethyl acetate. The ethyl acetate portion was washed with water, dried (MgSO$_4$), and concentrated to give a mixture of 1,3,3-trimethoxy-1-(isothiazoloxy-3-yl) propane and 1,3-dimethoxy-1,3-bis-(isothiazoloxy-3-yl) propane as an oil.

The girondalone compounds were separated by column chromatography on silica gel by first eluting with ethyl acetate to give 2.7 g 1,3,3-trimethoxy-1-(isothiazoloxy-3-yl) propane followed by methanol to elute 1,3-dimethoxy-1,3-bis-(isothiazoloxy-3-yl) propane (2.5 g.).

NMR (d$_6$-acetone) 8.6(1H), 6.2(1H), 5.7(1H), 4.5(1H), 3.3(9H), 2.0(m, 2H) 8.7(2H), 6.3(2H), 5.7(1H), 5.4(1H), 3.3(6H), 2.0–2.7(m,2H).

EXAMPLE 2

1,3,3-Trimethoxy-1-(5-chloro-isothiazoloxy-3-yl) Propane and 1,3-Dimethoxy-1,3-bis-(5-chloro-isothiazoloxy-3-yl) Propane To a stirred mixture of 5-chloro-3-hydroxy-isothiazole (2 g., 0.0148 m) and malonaldehyde bis (dimethyl acetal) (3.42 g., 0.0209 m), propionic acid (0.12 g., 0.0020m) was added. The mixture was heated at 100 ° C. with stirring for 12 hours, then cooled and poured into saturated sodium bicarbonate solution. The mixture was extracted with ethyl acetate. The ethyl acetate portion was washed with water, dried (MgSO$_4$), and concentrated. The girondalone products were separated by column chromatography using ethyl acetate:-hexane(1:1) as eluant to yield 0.44 g. of 1,3,3-trimethoxy-1-(5-chloro-isothiazoloxy-3-yl)propane as an oil and 0.80 g. of 1,3-dimethoxy-1,3-bis-(5-chloro-isothiazoloxy-3-yl) propane as a solid; mp 57° C.

NMR (d$_3$-chloroform) 6.3(1H), 5.8(1H), 4.6(1H), 3.4(9H), 2.1 (m,2H) 7.4(1H), 6.4(1H), 5.9(1H), 5.7(1H), 3.5(6H), 2.4 (m,2H).

EXAMPLE 3

Biological Activity

Efficacy against bacteria and fungi was carried out. A minimum inhibitory concentration (MIC) value was obtained using Trypticase Soy Broth, pH 7.0 and preparing a serial dilution with a starting concentration of 500 ppm. A stock solution of the test compound was made in dimethyl sulfoxide/acetone/water mixture. The test organisms used to demonstrate biocidal activity are listed in Table 1. The MIC's of the compounds of this invention against the test organisms are shown in Table 2. The tests were repeated with the media being adjusted to pH 5, 7, and 8.5. The results are shown in Tables 3 and 4. The following girondalones were evaluated:

1.) 1,3,3-Trimethoxy-1-(5-chloro-isothiazoloxyl-3-yl) propane;

2.) 1,3-Dimethoxy-1,3-bis-(5-chloro-isothiazoloxy-3-yl) propane;
3.) 1,3,3-Trimethoxy-1-(isothiazoloxy-3-yl) propane; and
4.) 1,3-Dimethoxy-1,3-bis-(isothiazoloxy-3-yl) propane

TABLE 1

Microorganisms used in the Antimicrobial Test

| Name | Abbreviations Used |
|---|---|
| Bacteria | |
| *Pseudomonas aeruginosa* | Psae |
| *Escherichia coli* | Ecol |
| *Staphlococcus aureus* | Saur |
| Fungi | |
| *Aspergillus niger* | Anig |

TABLE 2

| | MIC Values (um) | | | | | | |
|---|---|---|---|---|---|---|---|
| | Psae | | Ecol | | Saur | | Anig |
| Compound | M9G | TSB | M9G | TSB | TSB | TSB | TSB |
| 1 | 0.11 | 0.22 | 0.01 | 0.06 | <.0.001 | 0.011 | 0.01 |
| 2 | 0.08 | 0.16 | 0.04 | 0.08 | <0.001 | 0.01 | 0.02 |
| 3 | 0.50 | 0.25 | 0.13 | 0.13 | 0.06 | 0.06 | 0.50 |
| 4 | 0.37 | 0.05 | 0.10 | 0.19 | 0.01 | 0.02 | 0.75 |

TABLE 3

MINIMUM INHIBITORY CONCENTRATION (μm)

| | *Pseudomonas aeruginosa* | | | *Staphylococcus aureus* | | |
|---|---|---|---|---|---|---|
| | pH | | | | | |
| Compound | 5 | 7 | 8.5 | 5 | 7 | 8.5 |

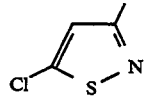

| 1 | 0.23 | 0.44 | 0.44 | 0.11 | 0.23 | 0.44 |
| 2 | 0.08 | 0.31 | 0.31 | 0.02 | 0.16 | 0.31 |

Top compound values: 0.06 | 0.24 | 0.47 | 0.03 | 0.24 | 0.92

TABLE 4

MINIMUM INHIBITORY CONCENTRATION (μm)

| | *Pseudomonas aeruginosa* | | | *Staphylococcus aureus* | | |
|---|---|---|---|---|---|---|
| | pH | | | | | |
| Compound | 5 | 7 | 8.5 | 5 | 7 | 8.5 |

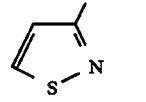

Top compound values: 0.32 | 0.32 | 1.24 | 2.48 | 2.48 | 2.48

| 3 | 1.00 | 2.01 | 2.01 | 0.13 | 0.50 | 1.00 |
| 4 | 1.50 | >1.50 | >1.50 | 0.19 | 0.37 | 0.10 |

Although specific embodiments and examples have been described herein, it should be born in mind that these have been provided by way of explanation and illustration and that the present invention is not limited thereby. Modifications which are within the ordinary skill in the art to make are considered to lie within the scope of the invention as defined by the following claims, including all equivalents.

What is claimed is:

1. Girondalone compounds of the formula I

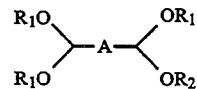

wherein

A is a residue of a dialdehyde of the formula

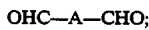

OHC—A—CHO;

$R_1$ is independently selected from the group consisting of $R_2$ and $(C_1-C_{18})$alkyl and;

$R_2$ is

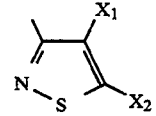

wherein (i) $X_1$ and $X_2$ can be joined to form a 5 or 6 membered fused carbocyclic ring, said ring being saturated, unsaturated, or aromatic; or (ii) $X_1$=Cl, H, methyl, or Br; and
$X_2$=H, Cl, or Br.

2. Compound according to claim 1 wherein said aldehyde is selected from the group consisting of glutaraldehyde; malonaldehyde; succinaldehyde; octanedial; 2,2-sulfonyl-bis-acetaldehyde; 2,2-oxy-bis-acetaldehyde; 2,2-alkylphosphine oxide-bis-acetaldehyde; succinic acid-2,3-bis-acetaldehyde; phthaldehyde; homophthalaldehyde; 4-octenedial; 2-cylopentene-1,4-dial; and glyoxal.

3. Compounds according to claim 1 wherein said compound is selected from the group consisting of 1,3,3-trimethoxy-1-(5-chloro-isothiazoloxy-3-yl) propane; 1,3-dimethoxy-1,3-bis-(5-chloro-isothiazoloxy-3-yl) propane; 1,3,3-trimethoxy-1-(isothiazoloxy-3-yl) propane; and 1,3-dimethoxy-1,3-bis-(isothiazoloxy-3-yl) propane.

4. Method of controlling undesirable microorganisms comprising introducing a girondalone compound according to claim 1 at, into, or onto a locus subject to attack by said microorganisms.

* * * * *